(12) United States Patent
Benning et al.

(10) Patent No.: US 8,766,568 B2
(45) Date of Patent: Jul. 1, 2014

(54) SYSTEM AND METHOD FOR MAINTAINING PERFORMANCE OF BATTERY-OPERATED TOOTHBRUSHES

(71) Applicant: Koninklijke Philips Electronics N.V., Eindhoven (NL)

(72) Inventors: Wolter Benning, Seattle, WA (US); Ari Lumbantobing, Issaquah, WA (US); Kevin Miller, Bellevue, WA (US)

(73) Assignee: Koninklijkle Philips N.V., Eindhoven (NL)

( * ) Notice: Subject to any disclaimer, the term of this patent is extended or adjusted under 35 U.S.C. 154(b) by 0 days.

(21) Appl. No.: 13/755,762

(22) Filed: Jan. 31, 2013

(65) Prior Publication Data
US 2013/0141020 A1  Jun. 6, 2013

Related U.S. Application Data

(63) Continuation of application No. 12/513,034, filed on Jan. 18, 2010, now Pat. No. 8,368,327.

(51) Int. Cl.
*H02P 1/00* (2006.01)
(52) U.S. Cl.
USPC .......................... 318/139; 318/114; 318/126
(58) Field of Classification Search
USPC ......................... 318/139, 114, 126
See application file for complete search history.

(56) References Cited

U.S. PATENT DOCUMENTS

| | | | |
|---|---|---|---|
| 5,189,751 A | 3/1993 | Giuliani et al. | |
| 5,493,747 A | 2/1996 | Inakagata et al. | |
| 5,613,259 A | 3/1997 | Craft et al. | |
| 5,994,855 A | 11/1999 | Lundell et al. | |
| 6,140,802 A | 10/2000 | Lundell et al. | |
| 2003/0233877 A1 | 12/2003 | Grez et al. | |
| 2007/0273331 A1 | 11/2007 | Cross et al. | |
| 2011/0273153 A1* | 11/2011 | Lepper et al. | 323/282 |

FOREIGN PATENT DOCUMENTS

| | | |
|---|---|---|
| JP | 07177932 | 7/1995 |
| WO | 0193776 A1 | 12/2001 |
| WO | 2006003617 A1 | 1/2006 |

\* cited by examiner

*Primary Examiner* — Karen Masih

(57) ABSTRACT

The system periodically measures the battery voltage of the toothbrush and the current in a stator portion of the motor for the appliance. The amplitude of movement of the toothbrush workpiece is determined from the measured stator current. A circuit/control program changes the duty cycle or pulse width of the drive signal from the motor if the battery voltage drops below a first threshold value and a circuit or control program changes the drive frequency of the appliance if the amplitude of the workpiece movement falls below a first threshold value. A circuit/control program terminates the operation of the toothbrush if the voltage drops below a second threshold value or if the amplitude drops below a second threshold value, both of which are less than the respective first thresholds.

11 Claims, 2 Drawing Sheets

SYSTEM AND METHOD FOR MAINTAINING PERFORMANCE OF BATTERY-OPERATED TOOTHBRUSHES

CROSS-REFERENCE TO RELATED APPLICATIONS

This is a continuation of and claims priority to Under 35 USC §120 from prior U.S. patent application Ser. No. 12/513,034, filed Nov. 2, 2007, which is a national application of PCT Application No. PCT/IB2007/054462, filed Nov. 2, 2007 and claimed the benefit of U.S. Patent Application 60/856,642, filed Nov. 3, 2006, the entire disclosures of which are incorporated herein by reference.

TECHNICAL FIELD

The invention relates generally to electric toothbrushes, and more particularly to a system for maintaining battery performance in such a toothbrush.

BACKGROUND OF THE INVENTION

Many personal care appliances, such as for example electric toothbrushes, are powered by replaceable batteries. One disadvantage of replaceable batteries is that battery voltage declines with discharge and use, with the voltage decreasing until the batteries finally die. Performance of the appliance begins to degrade significantly, however, well before the batteries actually die. Hence, there is a period of time during which, while the batteries are still operating, performance is adversely affected, which is undesirable. While all appliances with replaceable batteries have this functional disadvantage, even rechargeable batteries may have this disadvantage if their voltage declines between charging events.

It is thus desirable to be able to maintain battery voltage and thus consistent performance from replaceable and rechargeable batteries, above a specified threshold, in order to maintain a desired level of performance during the life of the appliance.

SUMMARY OF THE INVENTION

Accordingly one embodiment is a system for maintaining performance of an electric toothbrush powered by a battery, comprising: a system for measuring the battery voltage of the electric toothbrush and/or the current value in a stator portion of the motor for the electric toothbrush from which current value the corresponding amplitude of movement of the workpiece of the toothbrush is then obtained; a circuit/program routine for changing the duty cycle or pulse width for the drive signal of the motor if the battery voltage drops below a first voltage threshold value and/or a circuit/program routine for changing the drive signal frequency if the amplitude falls below a first amplitude threshold value, to increase the amplitude of movement of the workpiece; and a circuit/program routine for terminating the operation of the appliance if the battery voltage drops below a second voltage threshold value which is lower than the first voltage threshold value and/or if the workpiece amplitude drops below a second amplitude threshold value which is lower than the first amplitude threshold value.

Another arrangement is a system for maintaining performance of an electric toothbrush, powered by a battery, comprising: a system for measuring the battery voltage of the electric toothbrush; a circuit/program routine for changing the duty cycle or pulse width of the drive signal for the motor for the electric toothbrush if the battery voltage drops below a first threshold value; and a circuit/program routine for terminating the operation of the toothbrush if the voltage drops below a second threshold value which is lower than the first threshold value.

Still another arrangement is a system for maintaining performance of an electric toothbrush, powered by a battery, comprising: a system for measuring the current in a stator portion of a motor supplying a drive signal for the electric toothbrush and for determining the amplitude of movement of a brushhead workpiece from the measured stator current; a circuit/program routine for changing the drive frequency of the appliance if the amplitude of movement of the workpiece falls below a first threshold value, to increase the amplitude of the workpiece to maintain performance of the appliance; and a circuit/program routine for terminating the operation of the appliance if the amplitude of movement of the workpiece drops below a second threshold value which is lower than the first threshold value.

A still further aspect of the invention is a method for maintaining performance of an electric toothbrush powered by a battery, comprising the steps of: measuring the battery voltage of the electric toothbrush and/or the current in a stator portion of the motor for the electric toothbrush from which the amplitude of movement of the toothbrush is then obtained; changing the duty cycle or pulse width of the drive signal for the motor if the battery voltage drops below a first threshold value and/or changing the drive signal frequency of the appliance if the amplitude falls below a first amplitude threshold value to increase the amplitude of movement of the workpiece; and terminating the operation of the appliance if the battery voltage drops below a second voltage threshold value and/or if the workpiece amplitude drops below a second amplitude threshold.

A still further aspect of the invention is a method for maintaining performance of an electric toothbrush powered by a battery, comprising the steps of: measuring the battery voltage of the electric toothbrush; changing the duty cycle or pulse width of the drive signal for the motor for the electric toothbrush if the battery voltage drops below a first threshold value; and terminating the operation of the toothbrush if the voltage drops below a second threshold value which is lower than the first threshold value.

Another aspect of the invention is a method for maintaining performance of an electric toothbrush powered by a battery, comprising the steps of: measuring the current in a stator portion of a motor supplying the drive signal for the electric toothbrush and for determining the amplitude of movement of the brushhead workpiece from the measured stator current; changing the drive signal frequency if the amplitude of movement of the workpiece falls below a first threshold value, so as to increase the amplitude of the workpiece to maintain performance of the appliance; and terminating the operation of the appliance if the amplitude of movement of the workpiece falls below a second threshold value which is lower than the first threshold value.

BEST MODE FOR CARRYING OUT THE INVENTION

As discussed above, replaceable batteries in oral care appliances, such as electric toothbrushes, discharge over time, with the battery voltage decreasing with the discharge. In the present embodiment, at a selected time during operation of the appliance, the battery voltage and/or the current through the stator portion of the motor driving the appliance is determined. From that information, a characteristic of the motor drive signal, such as duty cycle, is adjusted to compensate for the decline in battery voltage or, in the case of an appliance with a resonant drive system, the drive frequency can be adjusted to increase the efficiency of the apparatus. These adjustments maintain performance of the appliance for a number of additional brushing events beyond which the decline in battery voltage would have resulted in degradation of performance below a minimum acceptable level.

Figure 1:
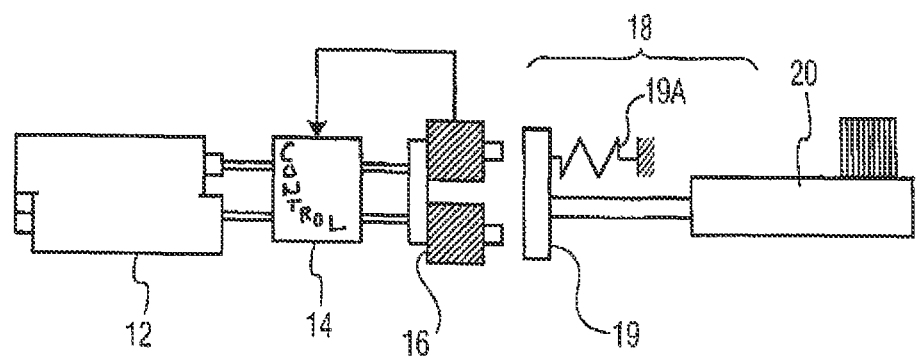
FIG. 1 is a block diagram showing the elements of a power toothbrush which incorporates the system described herein.

FIG. 1 shows a block diagram of an electric toothbrush. It includes replaceable batteries 12 and an electronic control unit 14. The electronic control unit 14 produces a drive signal which is applied to appliance stator 16 (motor), which drives a brushhead assembly 18 which for illustration includes a magnet arrangement 19 and a spring 19A. The brushhead assembly 18 includes a brushhead workpiece 20. The brushhead assembly 18 vibrates in a selected pattern, producing workpiece action for cleaning of teeth. A detailed description of one such embodiment is set forth in U.S. Pat. No. 5,189,751 the contents of which are hereby incorporated by reference. It should be understood, however, that such embodiment is illustrative of one electric power toothbrush; the invention disclosed herein is not limited to such an embodiment.

In a first arrangement of the present embodiment, which includes replaceable batteries, the drive system for the toothbrush is a resonant system, in which the frequency of the drive signal to the motor from the electronic control unit 14 is close to, if not the same as, the natural resonant frequency of the appliance. In this arrangement, control unit 14, which includes a microprocessor and a stored control program, measures the voltage from battery 12 and/or the current through stator 16 at a selected time during the lifetime of operation of the battery, after each brushing event or a specified number, e.g. 30, of brushing events. The control unit includes a standard algorithm which relates the value of the stator current to a corresponding amplitude of movement of brushhead workpiece 20, with amplitude being an indication of performance of the appliance.

Figure 2A:
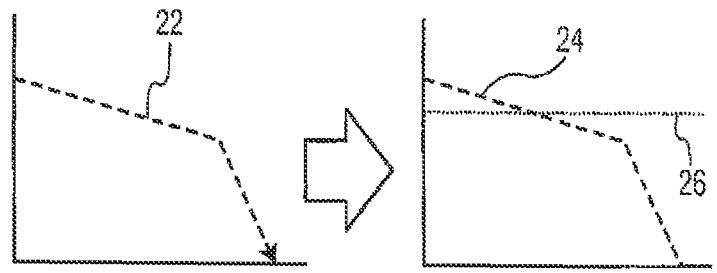
FIGS. 2A and 2B are diagrams showing the decline in voltage and performance over time relative to the number of brushings for an uncompensated appliance and similar diagrams for an appliance using the compensation system described herein.

The control unit 14 thus can have both battery voltage and workpiece amplitude to analyze. One or both of the following processes is then used to make adjustments which maintain the consistency of performance of the appliance even though the charge of the battery (and the battery voltage) has decreased. The action of an uncompensated arrangement is illustrated in FIG. 2A, which shows battery voltage 22 declining over a specific number of uses, with performance (amplitude) 24 also declining. The performance line 24 generally follows voltage line 22. In the embodiment shown, performance line 24 crosses a threshold value of acceptable performance 26 after a certain number of uses. Acceptable performance is generally defined as clinically effective results. FIG. 2A thus shows that performance is below an acceptable level for a time (a certain number of brushings) even though the appliance continues to operate before the battery voltage goes to zero, which prevents any further operation.

In a first mode, for a resonant drive system, the amplitude of movement of the brushhead workpiece (determined from the stator current) is compared with a first amplitude threshold. This is done, as indicated above, after each or a selected number of brushing events have occurred, for example in the range of 30-brushings, although this could vary, depending on the particular toothbrush and the battery. If the amplitude has fallen below a first threshold at that point, the drive frequency is adjusted to increase the efficiency of the toothbrush and hence the amplitude.

In this arrangement, during manufacture of the appliance, an initial drive frequency is established relative to the natural resonant frequency of the appliance such that the toothbrush is operating at an efficiency of less than 100%, i.e. in the range of 60-70%, for example. This leaves room for increasing efficiency by changing the drive frequency. Usually the difference between the two frequencies is in a range of up to 7 Hz.

Figure 2B:
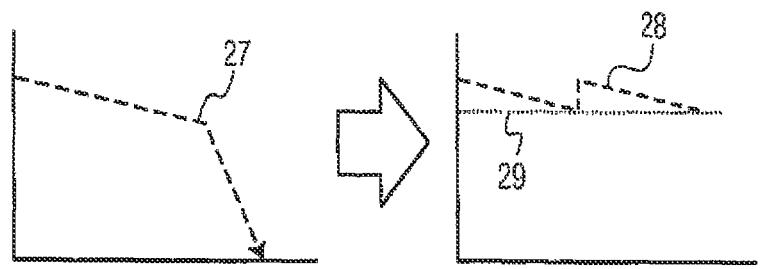
Figure 2C:
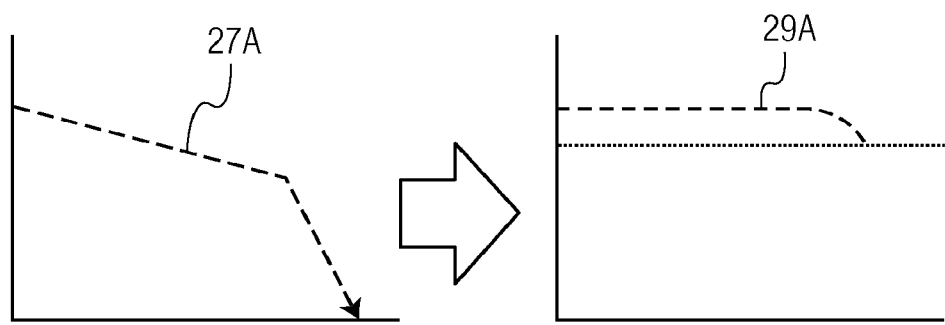
FIG. 2C is a diagram similar to FIGS. 2A and 2B showing multiple adjustments relative to performance.

When the amplitude of movement of the brushhead is below a first amplitude threshold, the drive frequency is changed so that an increase in operating efficiency results. This requires a slight (a few Hz) increase or decrease in the drive frequency, depending on the particular appliance. The increase in efficiency results in an increase in amplitude for a given battery voltage, maintaining desired performance of the toothbrush for an additional number of brushings, for example, in the range of 10-20 brushings. This is illustrated in FIG. 2B, in which, while the battery voltage still decreases, following line 27, the performance of the toothbrush shown by line 28 remains above the threshold line 29 for an extended period of time because of the increase in efficiency of the toothbrush occurring at least once during the life of the battery by a change in the drive frequency. FIG. 2C shows a generally flat performance curve 28A, in response to the typical voltage decline 27A, when there are multiple adjustments. While the present system maintains performance during decline in battery voltage, the system operates when factors in addition to battery voltage decline, such as component age, affect amplitude.

Figure 3:
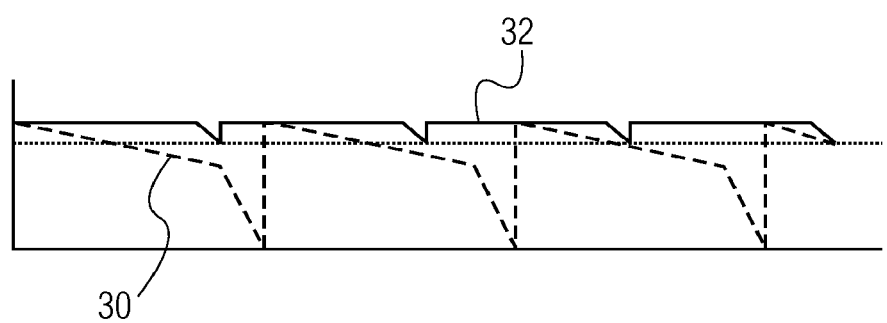
FIG. 3 is a diagram showing performance of an appliance over a portion of its lifetime for an uncompensated appliance and an appliance using the compensation system described herein.

FIG. 3 shows a diagram of brush performance over the life of a toothbrush, with the batteries being replaced periodically but still experiencing substantial periods of poor performance when the batteries discharge normally (line 30) as opposed to an appliance using the system described above (line 32), with several adjustments.

In addition to changing the drive frequency as a response to measurement of stator current and subsequent estimation of workpiece amplitude therefrom, the battery voltage itself can be evaluated after each or a selected number of brushing events relative to a first voltage threshold. If the measured voltage goes below the threshold, the duty cycle of the drive signal to the stator can be increased or, alternatively, the pulse width of the drive signal can be changed by pulse width modulation or similar technique. Both of these changes result in an effective increase in the voltage supplied by the control circuit. As described above, this adjustment can be done more than once during the lifetime of the batteries, until the duty cycle or the pulse width has reached its maximum adjustment.

The adjustment of the duty cycle or the pulse width of the drive signal can be used alone or combined with the change of drive frequency described above in resonant drive systems to increase the efficiency of the system, in order to maintain performance of the battery over an extended time, even though the battery voltage may steadily decrease during the lifetime of the battery.

It should be understood that the change in duty cycle or pulse width of the drive signal and the change in drive signal frequency can be accomplished in various ways, including by an electronic circuit or by a software program routine.

The above system extends the number of brushings possible from replaceable batteries at the desired level of performance for benefit of the user by improving the efficiency of the appliance, thereby reducing battery cost to the user while maintaining desired performance of the device over the extended number of brushings. The number of additional brushings will vary, depending upon the structure of the appliance, but one example is within the range of 10-20 additional brushings.

In addition to the above, in which adjustments are made when battery voltage and/or workpiece amplitude goes below first thresholds, the present invention will terminate operation of the appliance when the battery voltage declines below a second voltage threshold level and/or the workpiece amplitude declines below a second amplitude threshold level, at which point the battery can be replaced. For instance, relative to amplitude, if the amplitude declines below 8°, the operation of the brush will be terminated, while the drive frequency will be adjusted when the amplitude is below the first threshold but above the second threshold, 10° or 9° for example. The termination of operation can also be accomplished by a circuit or by a software program routine.

Hence, the above described embodiment adjusts the duty cycle/pulse width of the drive signal and/or adjusts the drive signal frequency to maintain performance of the appliance over an extended time, while terminating the operation of the brush when the voltage or amplitude declines below pre-established termination threshold levels, ensuring that the brush will always be effective as long as it is operating. As indicated above, however, the embodiment can be used with just the battery voltage determination/evaluation or the workpiece amplitude determination/evaluation.

Although the above embodiment generally describes a single adjustment to the drive signal, multiple adjustments prior to termination can be made, ultimately limited by the maximum values available in drive frequency, duty cycle and/or pulse width.

The above system can also be used for non-resonant drive systems, with just the battery voltage determination, resulting in change in the duty cycle and/or pulse width of the drive signal, with operation of the appliance being terminated when the voltage declines below a second selected threshold, at which point the battery can be replaced.

The compensation can also be time based, initiated by the installation of new batteries or charging of the batteries. If the appliance is characterized for normalized decline in performance over time, straightforward normalization compensation could be used. In such a case, when the number of uses in FIG. 2A is reached that corresponds with a pre-specified drop in performance, the duty cycle or drive frequency could be adjusted to compensate.

Hence, in summary, battery voltage and stator current can both be used, separately or in combination, to maintain performance of resonant drive system appliances, while battery voltage evaluation alone can be used for non-resonant systems.

While the above system is useful primarily for systems using replaceable batteries, to extend the number of brushings for a given battery, while maintaining consistent performance, the system can also be used for rechargeable batteries, to ensure performance of the system should the batteries decline in charge and voltage between chargings or if the components age sufficiently to affect performance. Hence, the invention is not limited to systems using replaceable batteries, nor is it limited to appliances using resonant drive systems, even though the system may find its primary use in such arrangements.

Hence, a system has been disclosed for maintaining consistent performance of the appliance which would otherwise decline battery voltage during discharge of the battery and resulting decrease in battery voltage.

Although a preferred embodiment of the invention has been disclosed for purposes of illustration, it should be understood that various changes, modifications and substitutions may be incorporated in the embodiment without departing from the spirit of the invention which is defined by the claims which follow.

What is claimed is:

1. A system for maintaining performance of an electric toothbrush powered by a battery, comprising:
    a system for measuring the battery voltage of the electric toothbrush and/or the current value in a stator portion of the motor for the electric toothbrush from which current value the corresponding amplitude of movement of the workpiece of the toothbrush is then obtained;
    a circuit/program routine for changing the pulse width of the drive signal for the motor if the battery voltage drops below a first voltage threshold value and/or a circuit/program routine for changing the drive signal frequency if the amplitude falls below a first amplitude threshold value, to increase the amplitude of movement of the workpiece; and
    a circuit/program routine for terminating the operation of the appliance if the battery voltage drops below a second voltage threshold value which is lower than the first voltage threshold value and/or if the workpiece amplitude drops below a second amplitude threshold value which is lower than the first amplitude threshold value.

2. The system of claim 1, wherein at least one adjustment is made to the drive signal pulse width and/or the drive frequency of the toothbrush during the lifetime of the battery.

3. The system of claim 1, wherein the battery is a replaceable battery.

4. The system of claim 1, wherein the battery is rechargeable.

5. The system of claim 1, wherein the drive frequency is adjusted within a range up to 7 Hz.

6. The system of claim 1, wherein the toothbrush is driven by a resonant system.

7. A method for maintaining performance of an electric toothbrush powered by a battery, comprising the steps of:
    measuring the battery voltage of the electric toothbrush and/or the current in a stator portion of the motor for the electric toothbrush from which the amplitude of movement of the toothbrush is obtained;
    changing the pulse width of the drive signal for the motor if the battery voltage drops below a first threshold value and/or changing the drive signal frequency of the appliance if the amplitude falls below a first amplitude threshold value to increase the amplitude of movement of the workpiece; and
    terminating the operation of the appliance if the battery voltage drops below a second voltage threshold value and/or if the workpiece amplitude drops below a second amplitude threshold.

8. The method of claim 7, wherein at least one adjustment is made to the drive signal pulse width and/or the drive frequency of the toothbrush during the lifetime of the battery.

9. The method of claim 7, wherein the battery is a replaceable battery.

10. The method of claim 7, wherein the drive frequency is adjusted within a range up to 7 Hz.

11. The method of claim 7, wherein the electric toothbrush is driven by a resonant system.

* * * * *